United States Patent
Feinberg et al.

(10) Patent No.: US 10,701,906 B2
(45) Date of Patent: Jul. 7, 2020

(54) SYSTEM, APPARATUS AND METHOD FOR NON-INVASIVE AVIAN EGG FERTILITY DETECTION

(71) Applicant: Egg Waves Ltd., Hod Hasharon (IL)

(72) Inventors: Ari Feinberg, Raanana (IL); Michael Arvanitis, Voula (GR)

(73) Assignee: Egg Waves Ltd., Hod Hasharon (IL)

( * ) Notice: Subject to any disclaimer, the term of this patent is extended or adjusted under 35 U.S.C. 154(b) by 0 days.

(21) Appl. No.: 16/313,450

(22) PCT Filed: Jun. 27, 2017

(86) PCT No.: PCT/IL2017/050714
§ 371 (c)(1),
(2) Date: Dec. 26, 2018

(87) PCT Pub. No.: WO2018/002922
PCT Pub. Date: Jan. 4, 2018

(65) Prior Publication Data
US 2019/0159433 A1    May 30, 2019

Related U.S. Application Data

(60) Provisional application No. 62/355,722, filed on Jun. 28, 2016.

(51) Int. Cl.
*A01K 43/04* (2006.01)
*G01N 33/08* (2006.01)
(Continued)

(52) U.S. Cl.
CPC ............ *A01K 43/04* (2013.01); *A01K 43/00* (2013.01); *G01N 33/08* (2013.01); *G01N 21/255* (2013.01); *G01N 2201/061* (2013.01)

(58) Field of Classification Search
CPC ....... A01K 43/04; A01K 45/007; G01N 33/08
See application file for complete search history.

(56) References Cited

U.S. PATENT DOCUMENTS

| | | | | |
|---|---|---|---|---|
| 4,656,479 A | * | 4/1987 | Kirimoto | G01S 13/76 342/147 |
| 5,173,737 A | * | 12/1992 | Mitchell | A01K 45/00 356/53 |

(Continued)

FOREIGN PATENT DOCUMENTS

WO    2016/005539 A1    1/2016

OTHER PUBLICATIONS

Alexis L. Romanoff, "Fertility Study of Fresh Eggs by Radio Frequency Conductivity and Dielectric Effect" (Year: 1939).*

(Continued)

*Primary Examiner* — Maurice C Smith
(74) *Attorney, Agent, or Firm* — Merchant & Gould P.C.

(57) ABSTRACT

A system, egg holding unit and methods are for non-invasively determining the fertility of an avian egg. The system includes an egg holding unit; at least one transmitter, operative for transmitting electromagnetic waves towards the at least one egg; and at least one receiver for receiving a received signal, including at least a portion of the electromagnetic waves after passing through the at least one egg placed within the egg holding unit. A processor is adapted to analyze the received signal according to a predetermined fertility determination procedure. A communication interface provides a fertility indication with respect to each one of the at least one egg. The communication interface may be coupled to a display device adapted to show fertilization data using a GUI, to one or more end users.

22 Claims, 9 Drawing Sheets

(51) Int. Cl.
*A01K 43/00* (2006.01)
*G01N 21/25* (2006.01)

(56) References Cited

U.S. PATENT DOCUMENTS

| | | | | |
|---|---|---|---|---|
| 6,029,080 | A | * | 2/2000 | Reynnells ............... A01K 45/00 356/52 |
| 6,234,320 | B1 | | 5/2001 | Hebrank |
| 6,845,253 | B1 | | 1/2005 | Schantz |
| 2005/0206876 | A1 | * | 9/2005 | Reeves ................. A01K 43/00 356/52 |
| 2006/0043177 | A1 | * | 3/2006 | Nycz .................... G06Q 10/087 235/385 |
| 2006/0082759 | A1 | * | 4/2006 | Hebrank ............... A01K 45/007 356/53 |
| 2007/0202223 | A1 | * | 8/2007 | Oren ...................... G01N 33/08 426/231 |
| 2010/0109938 | A1 | | 5/2010 | Oswald et al. |
| 2013/0044210 | A1 | | 2/2013 | Rozenboim et al. |
| 2015/0103624 | A1 | | 4/2015 | Thompson et al. |
| 2015/0138535 | A1 | | 5/2015 | Walukas et al. |
| 2016/0013831 | A1 | * | 1/2016 | Lea ........................ H01Q 21/24 455/562.1 |
| 2016/0100557 | A1 | * | 4/2016 | Adar ...................... A01K 43/00 119/322 |

OTHER PUBLICATIONS

Jiayu Song, "Two-Dimensional and Three-Dimensional NUFFT Migration Method for Landmine Detection Using Ground-Penetrating Radar" vol. 44, No. 6, Jun. 2006 (Year: 2006).*
Maksim Bano "Investigating alluvial and tectonic features with ground-penetrating radar and analyzing diffractions patterns" Journal of Applied Geophysics 43 2000 (Year: 2000).*
Mehdi Bahadorzadeh Ghandehari, "Electromagnetic Pulse Coupling inside a Rectangular Enclosure with an Aperture",SciRes, 2011 (Year: 2011).*
International Search Report and Written Opinion for PCT/IL2017/050714, dated Oct. 27, 2017.

* cited by examiner

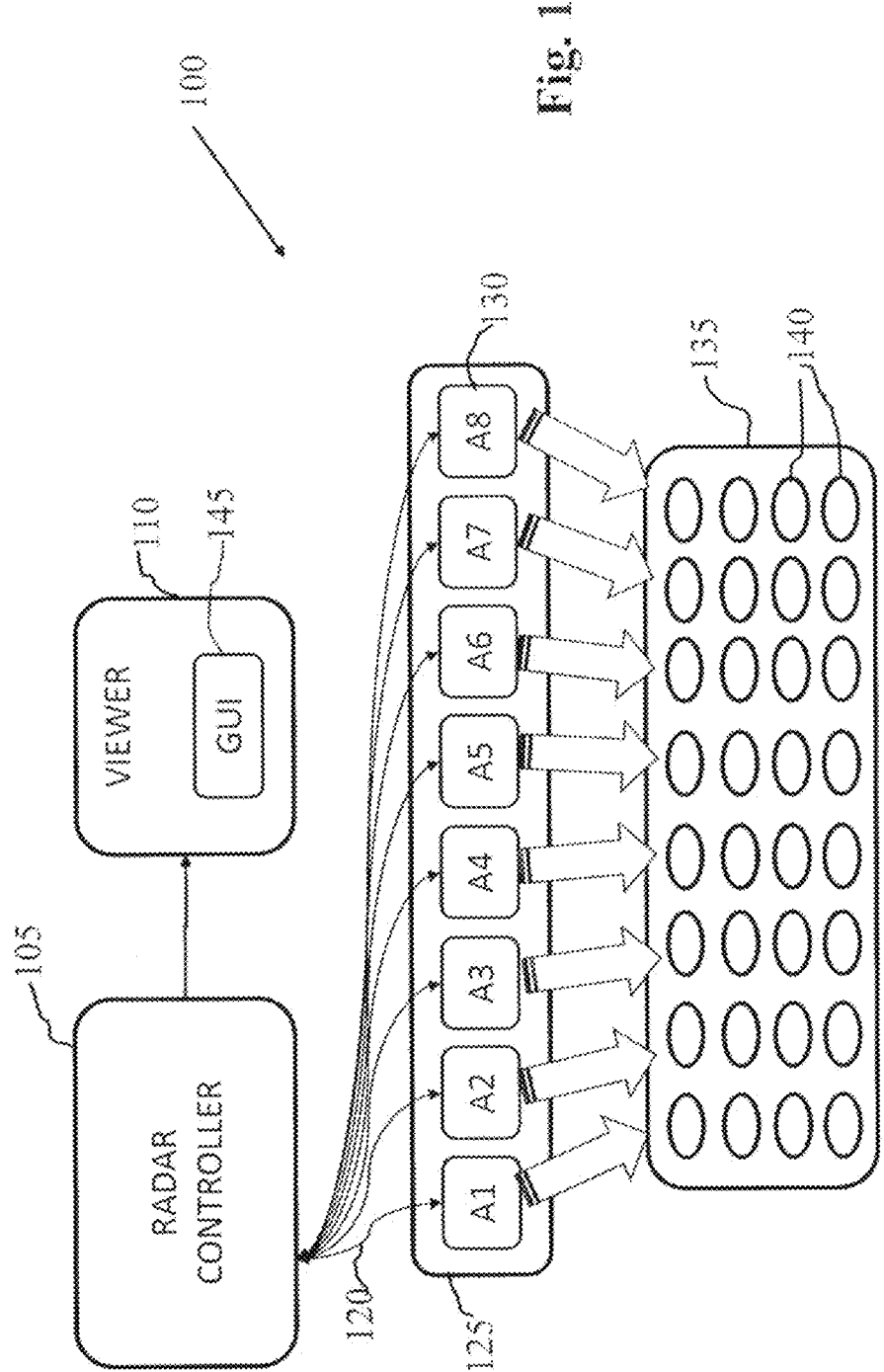

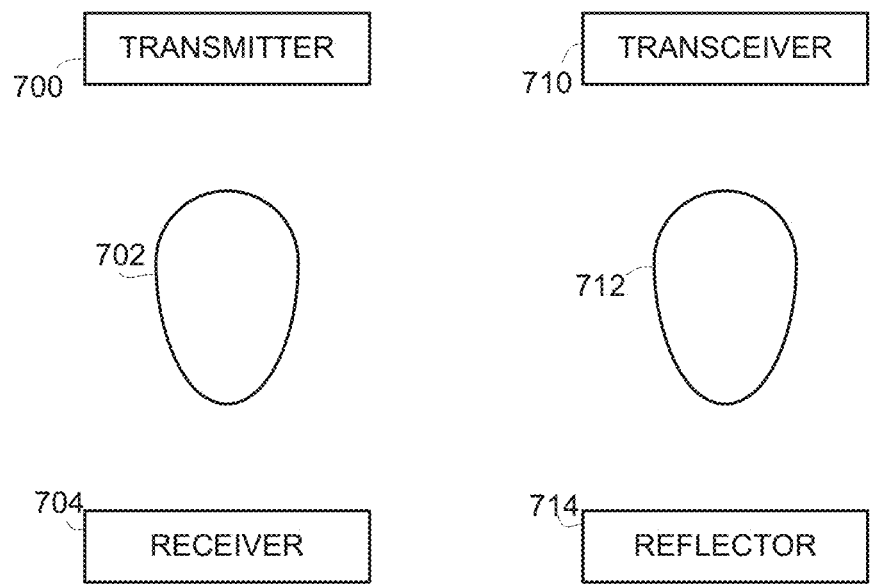
FIGURE 7A  FIGURE 7B
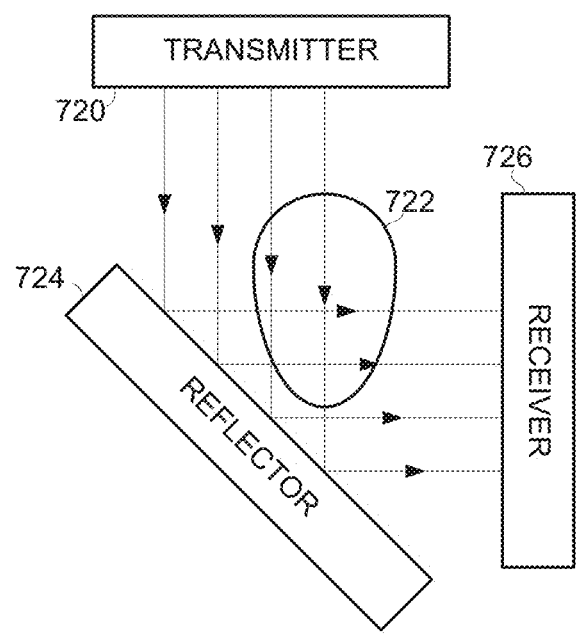
FIGURE 7C

SYSTEM, APPARATUS AND METHOD FOR NON-INVASIVE AVIAN EGG FERTILITY DETECTION

This application is a National Stage application of PCT/IL2017/050714, filed Jun. 27, 2017, which claims priority to U.S. Provisional Patent Application No. 62/355,722, filed Jun. 28, 2016, which applications are incorporated herein by reference. To the extent appropriate, a claim of priority is made to each of the above-disclosed applications.

FIELD OF THE DISCLOSED TECHNIQUE

The disclosed technique relates to systems and methods for classifying eggs, in general, and to systems and methods for non-invasive determination of the fertility condition of unhatched avian eggs, in particular.

BACKGROUND OF THE DISCLOSED TECHNIQUE

Hundreds of billions of eggs are produced annually in the world. After laying, the eggs are collected and transported to the hatchery and stored there at a low temperature until they are set in the incubator. It may take several days (up to seven days) until the eggs are placed in an incubator. Incubators hold thousands of eggs in a very controlled environment. In an industry of this size, efficient quality control and means for limiting production costs are vital. For example, a significant number of the eggs in a given hatchery are infertile. These eggs consume space and energy within the incubator, and can also cause contamination of other eggs. Usually, at day 16, the eggs are inspected by conventional methods to determine viability. A non-vial egg should be removed from the incubator in order to avoid contamination of other eggs. Thereafter, on the 21st day, the chicks hatch. A number of techniques have been developed for assessing the fertility of unhatched avian eggs.

For example, conventional technologies detect fertility of avian eggs, by using the $CO_2$ that is given off by the chick inside an egg, using MRI, measuring the amount of light transmitted by an egg, measuring modulation of a light signal passing through an egg due to motion, and thermographic methods that measure infrared light emitted by a live egg. Some of the conventional methods are described in U.S. Pat. Nos. 2,310,682, 4,788,427, 4,955,728, 5,696,325, 6,234,320, 6,722,201 and in US Patent Application Publication No. 2015/138,535.

Optical spectroscopic systems use absorption of light to measure egg fertility. Here to, since the blood vessels does not form until about two days after the egg is settled in the incubator, these methods cannot be used even in principle during the first day or two after the egg is settled in the incubator. In a matter of fact, blood vessels and the embryo can be clearly seen after a week in the incubator, and therefore only after this period of time the spectroscopic systems may obtain an effective result.

US Patent Application Publication No. 2003/200,932 issued to Toelken L. Taizo, entitled "Ultrasound quality inspection of avian eggs" discloses a method for making a quality determination in avian eggs, such as relating to fertility or hatching or hatchling viability. The method is performed after laying and before washing. A process line is equipped to process an endless succession of eggs at an early opportunity. The process line has an ultrasound inspection station for the eggs. The ultrasound inspection results are analyzed to make a finding correlatable to the egg's shell quality, which in turn is correlatable to such quality factors as fertility or hatching or hatchling viability. A sorting determination is made based on this analysis as to which output category the egg should be sorted. The output categories might number three or so including qualified premium as for graduation to hatchery operation, not qualified for hatchery but not waste, and flunked because unusable and hence waste. The intermediate category might include graded for pet consumption. The ultrasound inspection is operating on a 200 kHz frequency. The main drawback of ultrasound is that it can only penetrate the surface layer (i.e. very shallow penetration) and even for such penetration it is necessary to have an array of transceivers and receivers to scan a single egg. In addition, ultrasound is slow, the equipment must touch the egg's shell in order to receive the data and on top of that the results are affected by any dirt or other material accumulated on the shell of the egg.

U.S. Pat. No. 6,029,080 issued to Richard D. Reynnells et al. entitled "Method and apparatus for avian pre-hatch sex determination" discloses a non-invasive method and apparatus for sexing members of the avian species in the egg. The method uses nuclear magnetic resonance to determine whether the live embryo within an egg contains male or female sex organs. The method can further distinguish viable eggs from non-viable eggs. The method provides for sex determination of the embryo after removal from the setter incubation and prior to delivery to the hatching incubators. The apparatus can further sort eggs into a third group comprising eggs which are unusable.

A further procedure includes using a multivariate analysis method for detection of egg fertility. This method is also incapable of monitoring the embryo within the first day after the egg is settled in the incubator. The primary disadvantage of all of the above disclosed methods is that they cannot provide a reliable measure of egg fertility until at least several days after the egg has been settled in the incubator. Further the costs and time required to perform these checks has proven prohibitive. Furthermore, eggs which have been detected as non-fertile during the incubation stage are no longer safe for consumption and need to be discarded.

Even though a fertile egg already contains 40-60,000 cells at the moment of laying, none of the non-invasive methods yet developed can detect egg fertility that early. Thus, a non-invasive method for detecting avian egg fertility on the day of laying, or very soon thereafter, is needed. Moreover, it would be advantageous to have a system and method for determining fertility of eggs before eggs are transported for incubation while avoiding contact with eggs. There is a need for a procedure that may be executed in line and before transferring the eggs to incubators thereby minimizing loss of time, money and productivity.

SUMMARY OF THE PRESENT DISCLOSED TECHNIQUE

It is an object of the disclosed technique to provide a novel system, apparatus and non-invasive method for detecting the fertility condition of an egg very soon after laying and before the egg goes into the hatching and incubator process. The disclosed technique utilizes radar scan data obtained from the eggs and processes the received waves by at least removing at least one of the following: airwave, hyperbola and ringing in order to obtain an indication of a fertile or of a non-fertile egg for each of the scanned eggs.

In accordance with the disclosed technique, there is thus provided a system for non-invasively determining the fertility of an avian egg. The system comprises: an egg holding unit in which at least one egg is positioned; at least one transmitter, operative for transmitting electromagnetic waves towards the at least one egg; at least one receiver for receiving a received signal, including at least a portion of the electromagnetic waves after passing through the at least one egg placed within the egg holding unit; a processor adapted to analyze the received signal according to a predetermined fertility determination procedure; and a communication interface for providing a fertility indication with respect to each one of the at least one egg.

In a further embodiment of the disclosed technique the communication interface for providing a fertility indication with respect to each one of the at least one egg is coupled with a display device operative to show fertilization data obtained from said processor. According to another embodiment of the disclosed technique the display device uses a graphical user interface (GUI) and provides said fertilization data to one or more end users. In a yet further embodiment of the disclosed technique the system further includes means coupled with the communication interface, operative for digital and/or mechanical marking at least some of the at least one egg scanned by the system. The marking indicates fertility or non-fertility of the egg. An additional embodiment of the disclosed technique includes a system in which the at least one transmitter is coupled with at least one antenna. A further embodiment of the disclosed technique includes a system including at least one reflector, operative to reflect at least a portion of the electromagnetic waves towards the at least one receiver. Yet, in a further embodiment of the disclosed technique the at least one reflector is planar. Alternatively, in another embodiment of the system the at least one reflector is curved.

A yet further embodiment of the disclosed technique is directed to an egg holding unit constructed for containing at least one egg. The egg holding unit comprises an outer casing and an inner casing. The egg holding unit is adapted to selectively reflect radar signals from the eggs to at least one radar transceiver array collecting electromagnetic wave reflection from multiple eggs. The inner casing of the egg holding unit is made of non-conductive materials such as glass, fiberglass, porcelain, plastic, wood, lignocellulosic fibrous material (pulp paper), rubber etc.

Another aspect of the disclosed technique is a non-invasive method for detecting the fertility condition of an avian egg. The method comprises the steps of radar scanning at least one egg, wherein at least one radar transmitter transmits waves and at least one radar receiver receives at least a portion of the waves after passing through the at least one egg thereby obtaining a received scan signal; processing the received scan signal which includes at least portion of the waves, to determine a fertility indication for the at least one egg. The processing of the received scan signal includes removal of unwanted signals from the received scan signal thereby outputting a filtered signal; and analyzing said filtered signal to determine correlation with at least one reference marker evidencing fertility or non-fertility of an egg to determine a fertility condition. The unwanted signals comprising at least one of airwaves, environmental noise and ringing. In addition to the removal of unwanted signals, it is also possible to remove hyperbolas. Subsequent to the processing step, the final step of the method is providing a fertility indication for each egg scanned.

A further embodiment of the disclosed method comprises removal of unwanted signals from the received scan signal wherein the removal step includes: removing airwaves, removing hyperbolas, removing ringing. Yet an additional embodiment of the method includes removing airwaves from the received scan signal by using time zero correction. In an additional embodiment of the method removing hyperbolas from the received scan signal is obtained by using migration. In a further embodiment of the method removing ringing from the received scan signal is obtained by using IIR filters (bandpass, background removal, stacking) or deconvolution filtering. In a preferred embodiment of the disclosed technique the step of removing airwaves is carried out before the step of removing ringing. In additional embodiment of the disclosed method the step of removing ringing is carried out before or after the step of removing hyperbolas.

A further embodiment of the disclosed method comprises the step of providing a digital and/or mechanical fertility indication for each egg scanned. Additional embodiment of the disclosed method further comprises the step of displaying the eggs with fertility indication on one or more screens. Yet a further embodiment of the disclosed method includes the step of a user interacting with the egg processing machines to stop the machines, zoom in or out, mark an egg, remove an egg, add notes, and is send alerts.

BRIEF DESCRIPTION OF THE DRAWINGS

The principles and operation of the system, apparatus, and method according to the disclosed technique may be better understood with reference to the drawings, and the following description, it being understood that these drawings are given for illustrative purposes only and are not meant to be limiting, wherein:

FIG. 1 is a schematic block diagram illustration of a system for non-invasively determining the fertility of an avian egg, constructed and operative in accordance with an embodiment of the disclosed technique;

FIGS. 7A-7C are schematic illustrations of additional transmitter receiver configurations, constructed and operative in accordance with the disclosed technique.

Figure 2A:
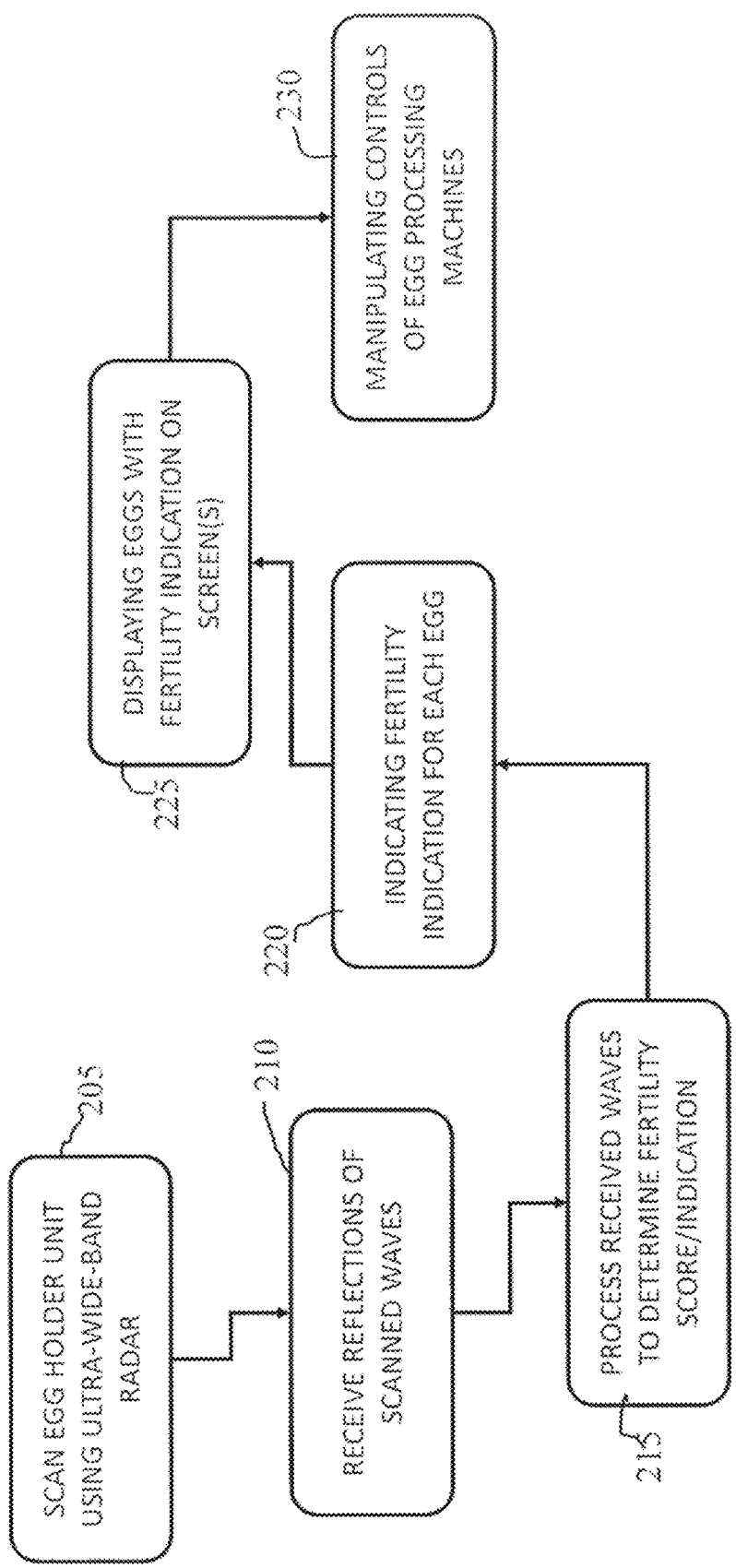
FIG. 2A is a flowchart illustrating a non-invasive method for detecting the fertility condition of an avian egg, constructed and operative in accordance with an embodiment of the disclosed technique.

It will be appreciated that for simplicity and clarity of illustration, elements shown in the drawings have not necessarily been drawn to scale. For example, the dimensions of some of the elements may be exaggerated relative to other elements for clarity. Further, where considered appropriate, reference numerals may be repeated among the drawings to indicate corresponding or analogous elements throughout the serial views.

DETAILED DESCRIPTION OF THE EMBODIMENTS

The disclosed technique overcomes the disadvantages of the prior art by providing system, egg holding unit and non-invasive method for detecting the fertility condition of an avian egg very soon after laying and before the egg goes into the hatching and incubation process. The disclosed technique utilizes electromagnetic (radar) data of certain frequency in order to determine fertility indication for each of the eggs.

Definitions

The term "egg" as used herein may encompass eggs or other objects with outer shells or covers that may be penetrated using radar technology.

Radar, short for "Radio Detection And Ranging" is an object-detection system that uses radio waves to determine the range, angle, or velocity of objects. It is typically used to detect aircraft, ships, spacecraft, guided missiles, motor vehicles, weather formations, and terrain. A radar transmits radio waves or microwaves that reflect from any object in their path. A radar subsequently receives and processes these reflected electromagnetic waves to determine properties of the object(s) detected. The term "radar" as used herein may encompass all terms of Radio Detection and Ranging.

The term "ultra-wide-range" as used herein refers to an ultra-wide spectrum of frequencies, for example from 300 MHz and 4 GHz. The term "airwave" as used herein refers to a reflection created due to radar energy forwarded directly from the Transmitter to the Receiver (through Air) and does not penetrate into the object that is being scanned. The term "hyperbola" refers to a signal created while the antennas vertically scan a target. A hyperbola is created as an indication of the target.

The term "ringing" used herein, refers to multiple occurrences of noise that is caused for a given signal by a very fast medium (e.g. when the electromagnetic wave travels through air, because air has a low dielectric of 1, the reflection that we get from the air is multiple times the one we get from other targets and this creates a series of noise lines in the data that may obscure other targets than air). The term "fertility" as used herein may encompass the quality of being fertile or productive, and for eggs, the property of having a live animal organism in the early stages of growth in the egg.

Non-limiting embodiments of the disclosed technique include an electromagnetic non-invasive fertility detection system that can be used to detect if eggs are fertile or not. The fertility detection system uses one or multiple Ultra-wide band radar antennas functioning at a certain frequency to get reflection signals from multiple eggs at the same time. The signals are processed to determine fertility indication. Fertility indication is estimated based on at least one of the reflection patter, a derivative of the reflection pattern, polarity of the signal, dielectric value of the core of the egg and a database including reference data of fertile and infertile eggs. The system can establish in near real-time, and with probability larger than 90%, whether the eggs are fertile or not.

The fertility detection system enables detection of egg fertility soon after laying, for example, on day 0, day 1 or later. Thus, the fertility of the egg can be determined before the egg goes into the hatching and incubator process. The near real time procedure may be executed in line, to enhance the efficiency of the detection process, to substantially minimize loss of time and productivity. In this way, the eggs producer can save substantial eggs, time and resources.

Reference is now made to FIG. 1 which is a schematic block diagram illustration of a system for non-invasively determining the fertility of an avian egg, constructed and operative in accordance with an embodiment of the disclosed technique. Fertility determining system 100 includes a radar controller 105, which is a processor adapted to operate at least one radar transceiver array and analyze electromagnetic waves received from the scanned eggs according to a predetermined fertility determination procedure (algorithm). Radar controller 105 includes memory, executable code, and relevant radar controlling software, for example, to program and execute an egg fertility detection function. Radar controller 105 is connected via connectors 120 to a radar transceiver array 125, which includes multiple signal transceivers 130 (referenced as A1 to A8). In an embodiment of the disclosed system, the signal transmitters and antennas/receivers may be integrated into a single transceiver module, while in an alternative embodiment of the disclosed system these units (transmitter and antenna/receiver) may be in separate modules.

Yet, another embodiment of radar transceiver array 125 may include separate transmitters and receivers such that for example, A1 is a transmitter (as well as A3, A5 and A7) and A2 is a receiver (as well as A4, A6 and A8). Transceivers 130 may be analog and/or digital transceivers. An embodiment of the disclosed technique provides a system with up to eight different antennas of either same or different frequency providing additional data in respect of the scanned eggs. In some embodiments of the disclosed technique, a digital antenna may be used that is designed to integrate stacking technology, to help improve the depth and data resolution performance of the transceivers. Optionally, radar controller 105 further includes a communication interface for providing the fertility indication to any equipment coupled therewith with respect to each scanned egg. Such a communication interface may be coupled with a user interface presenting to the user visual or audible egg fertility indications. An example for a communication interface coupled to a GUI is shown in FIG. 1, referenced as viewer 110. Alternatively, such a communication interface may be coupled with an egg marking instrument such as, but not limited to:

- A printer (e.g., an inkjet printer), printing symbols on a selected egg, using conventional ink or modified ink (e.g., metal enhanced ink, phosphorous ink).
- A label provider, attaching labels to a selected egg.
- A physical modifier, modifying at least a portion of a selected egg (e.g., a laser generator burning marks on the shell of a selected egg).

Figure 3A:
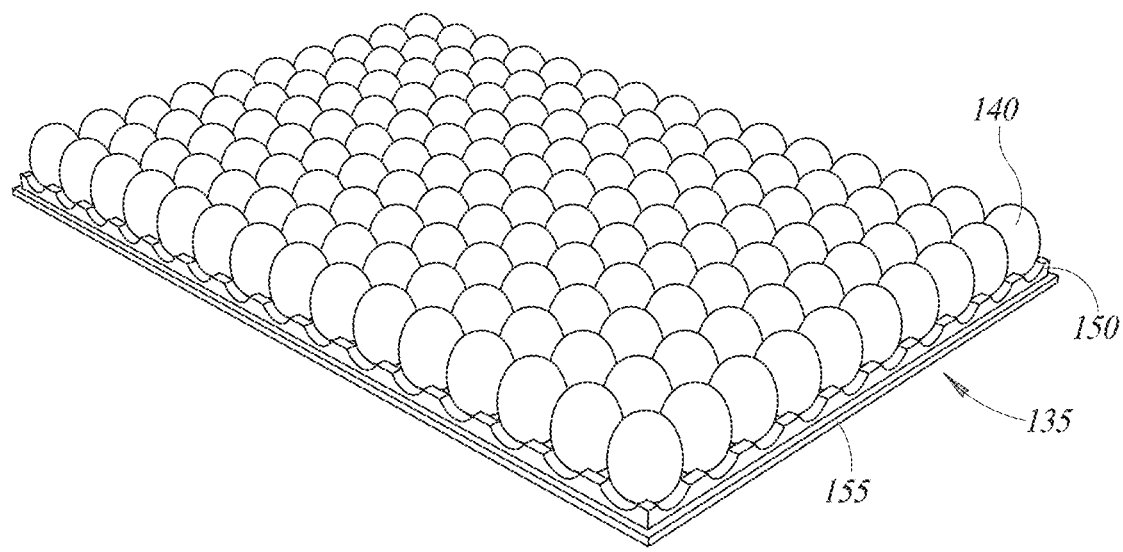
FIG. 3A is a top/side perspective view of an egg holding unit, is constructed and operative according to an embodiment of the disclosed technique.
Figure 3B:
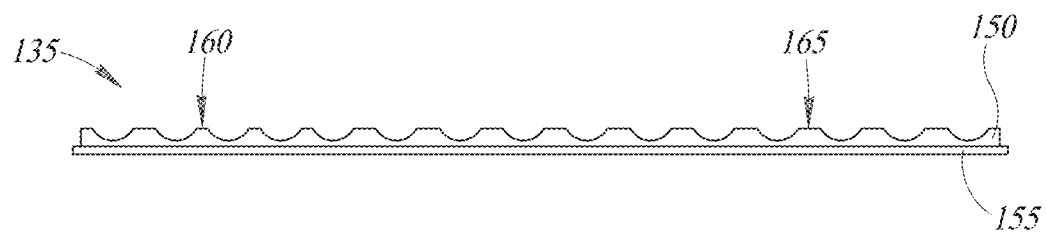
FIG. 3B is a cross-sectional side view of an egg holding unit, constructed and operative according to an embodiment of the disclosed technique.

Radar transceiver array 125 is operative to transmit selected radar signals towards one or more target eggs 140 to be detected. For the ease of understanding, reference is also made to FIGS. 3A and 3B which depict an egg holding unit constructed and operative in accordance with an embodiment of the disclosed technique. Eggs 140 may typically be configured or positioned in an egg holding unit 135, which will be configured to hold one or more eggs in a desired position, with selected spacing between them (for example, partitions 160 (which are narrower) or partitions 165 (which are wider), in FIG. 3B), with a selected number of rows and columns of eggs. Egg holding unit 135 is optionally placed on an electric conveyor and then conveyed to radar scanning by the system. The scanning is carried out before eggs are transported for incubation, and preferably this procedure is executed in line. Egg holding unit 135 is adapted to selectively reflect radar signals from eggs 140 to at least one radar transceiver array 125 for processing by radar controller 105. In some embodiments egg holding unit 135 may be comprised from materials and/or structures that optimally facilitate radio wave reflections. For example, materials may be used that are non-conductive, so as to substantially not interfere with the radar signals. For example, materials such as glass, fiberglass, porcelain, plastic, wood, lignocellulosic fibrous material (pulp paper) and rubber may be used in the egg holding unit 135.

In some embodiments, egg holding unit 135 is provided with an outer casing 155 and an inner casing 150 (shown in FIGS. 3A and 3B) for facilitating the collecting of electromagnetic wave reflections from multiple eggs within the egg holder. Inner casing 150 and outer casing 155 may be produced each from a different material, and optionally designed to improve the reflected signals such that the reflected signals contain less unwanted signal portions. For example, outer casing 155 can be produced from metallic material or include metallic elements. However, inner casing 150 is manufactured from non-conductive material such as non-conductive materials such as glass, fiberglass, porcelain, plastic, wood, lignocellulosic fibrous material (pulp paper), rubber etc. For example, embodiments of the outer casing of the egg holding unit include flat casing, casing which is not flat and a casing with embedded wires or casing made from matrix material having metal elements positioned below the core of the egg. In general, radar transceiver array 125, will receive reflected electromagnetic waves from eggs 140, which can then be received by transceivers 130. The signals are then sent to the radar controller 105 for processing, for example, to determine in near real-time whether a target egg is fertile or not fertile.

According to some embodiments, the radar transceivers may be configured and spaced according to a user's requirements, to optimally scan the target or targets being detected. At least one radar transceiver array is positioned above the egg holding unit, however in some embodiments of the system according to the disclosed technique, several arrays can be positioned around the eggs in such a configuration that an effective scan of the eggs is enabled. This configuration should account for the type of waves being transmitted and received, the number and size of the object(s) being detected, the required functionality or goals of the detection etc. In one example, each radar transceiver may view a range of around 0-90 degrees therefore in some configurations may view a range of around 1-40 cm wide (it depends on the distance between transmitter and eggs), and around 80 cm deep or less, thereby being able to effectively scan one or more eggs in an egg holder unit. It should be emphasized here that contrary to different methods that require a direct contact with the shell of the egg, the disclosed technique is able to provide fertility determination contactless. Preferably, the antennas are located in a distance of up to 40 cm above the eggs. When using multiple antenna in either the transmitting end or the receiving end, the relative polarity (i.e., either between the antennas at the transmitting end, or between the antennas in the receiving end or between antennas at the transmitting end relative to those at the receiving end) can be modified in order to optimize coverage, beam formation, focus, gain and the like, either spatially or electronically and in each such case, either manually or automatically.

According to some embodiments, the radar transceivers may be ground coupled radars, however other radar types may be used. According to some embodiments, the transceiver array may be connected to a control unit that can be proximate to the transceivers, or distanced from the receivers. In some embodiments, Ultra high frequency (UHF) radar, optionally defined by frequencies ranging between 300 MHz and 4 GHz may be used for scanning avian eggs. For example, UHF radar may be used to view targets at very high resolution, and to limit the effective range of wave delivery to penetrate the target objects in a typical facility. In further embodiments, L band radar, typically defined by frequencies ranging between 1 and 2 GHz may be used for scanning avian eggs. In still further embodiments, S band radar, typically defined by frequencies ranging between 2-4 GHz may be used for scanning avian eggs. In yet further embodiments, a radar signal may be used that peaks at around 2.4 to 2.8 GHZ, or more specifically at around 2.6 GHZ. A signal range may typically be used to enable a wide range of signals to be delivered simultaneously. Of course, other signal strengths, lengths, sizes etc. may be used. In some embodiments, multiple radar transceivers may be used to enable cross signals to be reflected and processed, thereby providing additional data relating to egg fertility or other relevant egg conditions. In some embodiments, multiple radar transceivers may be used to enable 3D signals to be reflected and processed, thereby providing additional data relating to egg fertility or other relevant egg conditions.

Figure 6A:
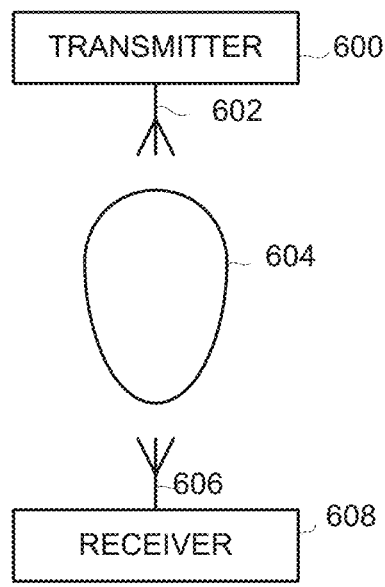
FIGS. 6A-6D are schematic illustrations of various transmitter receiver configurations, constructed and operative in accordance with the disclosed technique.

Reference is further made to FIGS. 6A-6D, which are is schematic illustrations of various transmitter receiver configurations, constructed and operative in accordance with the disclosed technique. FIG. 6A discloses a transmitter 600 associated with a receiver 608. Transmitter 600 is coupled with a single transmit antenna 602, for transmitting electromagnetic signals through an egg 604. After passing through egg 604, at least a portion of these electromagnetic signals are received by single receive antenna 606, which is coupled with receiver 608.

Figure 6B:
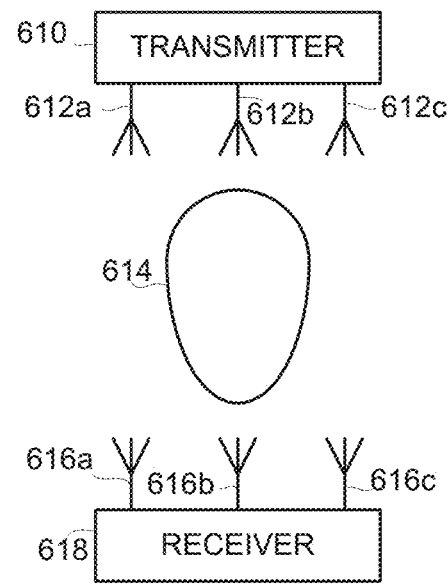

FIG. 6B discloses a transmitter 610 associated with a receiver 618. Transmitter 610 is coupled with an array of transmit antennas 612a, 612b and 612c, for transmitting electromagnetic signals through an egg 614. After passing through egg 614, at least a portion of these electromagnetic signals are received by an array of receive antennas 616a, 616b and 616c, which are coupled with receiver 618. Transmitter 610 may transmit an identical signal through each of transmit antennas 612a, 612b and 612c or alternatively, a separate unique signal through each of them. Transmitter 610 may also coordinate the phase of each of these signals to form different special configurations of transmitted electromagnetic signals.

Figure 6C:
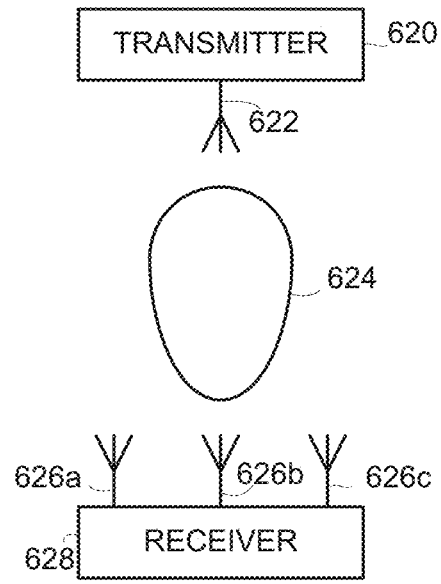

FIG. 6C discloses a transmitter 620 associated with a receiver 628. Transmitter 620 is coupled with a single transmit antenna 622, for transmitting electromagnetic signals through an egg 624. After passing through egg 624, at least a portion of these electromagnetic signals are received by an array of receive antennas 626a, 626b and 626c, which are coupled with receiver 628.

Figure 6D:
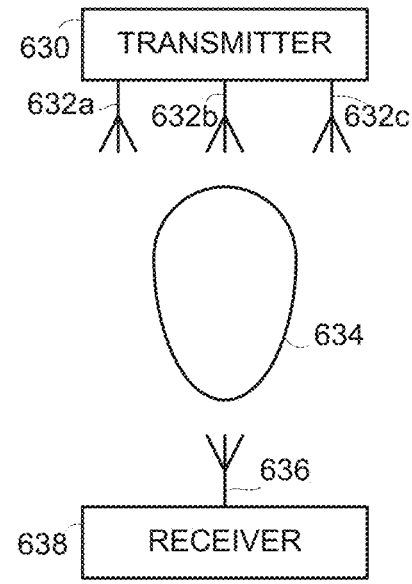

FIG. 6D discloses a transmitter 630 associated with a receiver 638. Transmitter 630 is coupled with an array of transmit antennas 632a, 632b and 632c, for transmitting electromagnetic signals through an egg 634. After passing through egg 634, at least a portion of these electromagnetic signals are received by a single receive antenna 636, which is coupled with receiver 638. Similar to FIG. 6B, transmitter 630 may transmit an identical signal through each of transmit antennas 632a, 632b and 632c or alternatively, a separate unique signal through each of them. Transmitter 630 may also coordinate the phase of each of these signals to form different special configurations of transmitted electromagnetic signals.

Reference is further made to FIGS. 7A-7C, which are schematic illustrations of additional transmitter receiver configurations, constructed and operative in accordance with the disclosed technique. FIG. 7A discloses a transmitter-receiver configuration in which a transmitter 700 is located on one side of an egg 702 and a receiver 704 is located on the opposite side of egg 702. In this configuration, receiver 704 receives signals transmitted by transmitter 700, in which at least a portion of these received signals, passed through egg 702.

FIG. 7B discloses a transmitter-receiver configuration in which transmitter and receiver are combined into a single transceiver 710, located on one side of an egg 712. In this configuration, a reflector 714 is located on the opposite side of egg 712. Transceiver 710 transmits electromagnetic signals towards reflector 714, wherein at least a portion of these electromagnetic signals pass through egg 712. Reflector 714 reflects the electromagnetic signals that impinged thereon back towards transceiver 710, wherein at least a portion of these reflected electromagnetic signals, pass through egg 712. Transceiver 710 then detects the reflected electromagnetic signals. It is noted that such a reflector may be planar or curved, in accordance with a required reflection function.

FIG. 7C discloses a transmitter-receiver configuration in which a transmitter 720 is located on one side of an egg 722 and a receiver 726 is located on another side of egg 722, which is not directly across from transmitter 720. In the example presented in FIG. 7C, receiver 726 is located on a side of egg 722, which is diagonal from the side that transmitter 720 is locate on. The transmitter-receiver configuration of FIG. 7C further includes a reflector 724, which is spatially configured and located to receive electromagnetic signals transmitted from transmitter 720, and reflect them towards receiver 726, whereby at least a portion of these electromagnetic signals pass through egg 722. It is noted that such a reflector may be planar or curved, in accordance with a required reflection function.

Referring back to FIG. 1, there is illustrated an embodiment of the system in which the communication interface includes means for providing fertility or non-fertility indication for each egg represented by viewer 110. As stated above, radar controller 105 processes the scan signal received from the radar antenna or receiver. Post-processed signals can then be sent to one or more viewers 110, for example, a computer or screen for viewing the signals or a representation of the signals. Viewer 110 may be integrated into radar controller 105, or may be external to radar controller 105. In some cases, a viewer may be used for each transceiver, yet in other cases a single viewer may integrate the reflections received by multiple transceivers.

In some embodiments, advanced software processing may be used to provide enhanced images, graphics, colors, definitions etc. to viewer 110, delivered via Graphic User Interface (GUI) 145. In some embodiments, viewer 110 may include an input device, for example, a touch screen, mouse, keyboard etc., to manipulate the data displayed on GUI 145. Optionally, a list of non-fertile eggs can be produced by radar controller 105 and presented on viewer 110 in order to enable a user to handle detection or selection of non-fertile eggs.

An additional embodiment of the disclosed system includes indication means that provide marking options of the eggs whereas fertile or non-fertile eggs, according to the preferences of the user, are inked with respective color. Indication means may provide the fertility/non-fertility indication by dropping ink on the non-fertile eggs detected by the radar controller 105 facilitating removal of the eggs from the egg holding unit (or tray). In some embodiments the indication of fertile/non-fertile eggs is provided by a list indicating the positions in the egg holding unit of the identified eggs (fertile or non-fertile according to the desired mode selected by the user). For example, tray 1, egg in column 2, row 3, column 4, row 6 etc. Alternatively, each position on the tray has its own reference number and then the list includes only numbers: 11, 31, 44, 56 etc.

In accordance with some embodiments, the fertility detection system may be portable or stationary, and may scan in line at variable production speeds, or set up in alternative environments. Optionally, a stationary system may be provided with a laptop connection and respective software for remote controlling the system, if required. As soon as all components are connected and the control unit turns on, the user gets into the main screen where he can trigger the antennas and remotely observe detection results and operate the system. In some embodiments the fertility detection system can carry multiple antennas with adjustable spacing in between them, and adjustable settings that enable the user to handle detection of different numbers of eggs, in different environments, and in accordance with the detection needs. In accordance with some embodiments, the egg fertility detection systems described above may be used for various types of eggs.

FIG. 2A schematically illustrates a series of operations or processes that may be implemented to enable radar based non-invasive avian egg fertility detection, in accordance with some embodiments of the present invention. As can be seen in FIG. 2A, at step 205 the egg holder unit with eggs inside is scanned by a radar transceiver or transmitter, using ultra-wide-band radar signals. At step 210, reflections of scanned waves are received by the radar antenna or receiver. At step 215, received waves are processed to determine a fertility score/indication for each egg scanned, individually or in a group. At step 220 the fertility indication is digitally and/or mechanically marked for each egg, whether in software and/or a physical marking. At step 225 eggs with their fertility indications may be displayed on one or more screens. At step 230 various egg processing elements, such as people, machines, robots etc. may be manipulated, controlled or managed using the radar scanning system. In one example, the user may interact with the egg processing machines using controls entered into the GUI on the screen (s), for example, to stop the machines, zoom in or out, mark an egg, remove an egg, add notes, send alerts, etc. Any combination of the above steps may be implemented. Further, other steps or series of steps may be used.

Figure 2B:
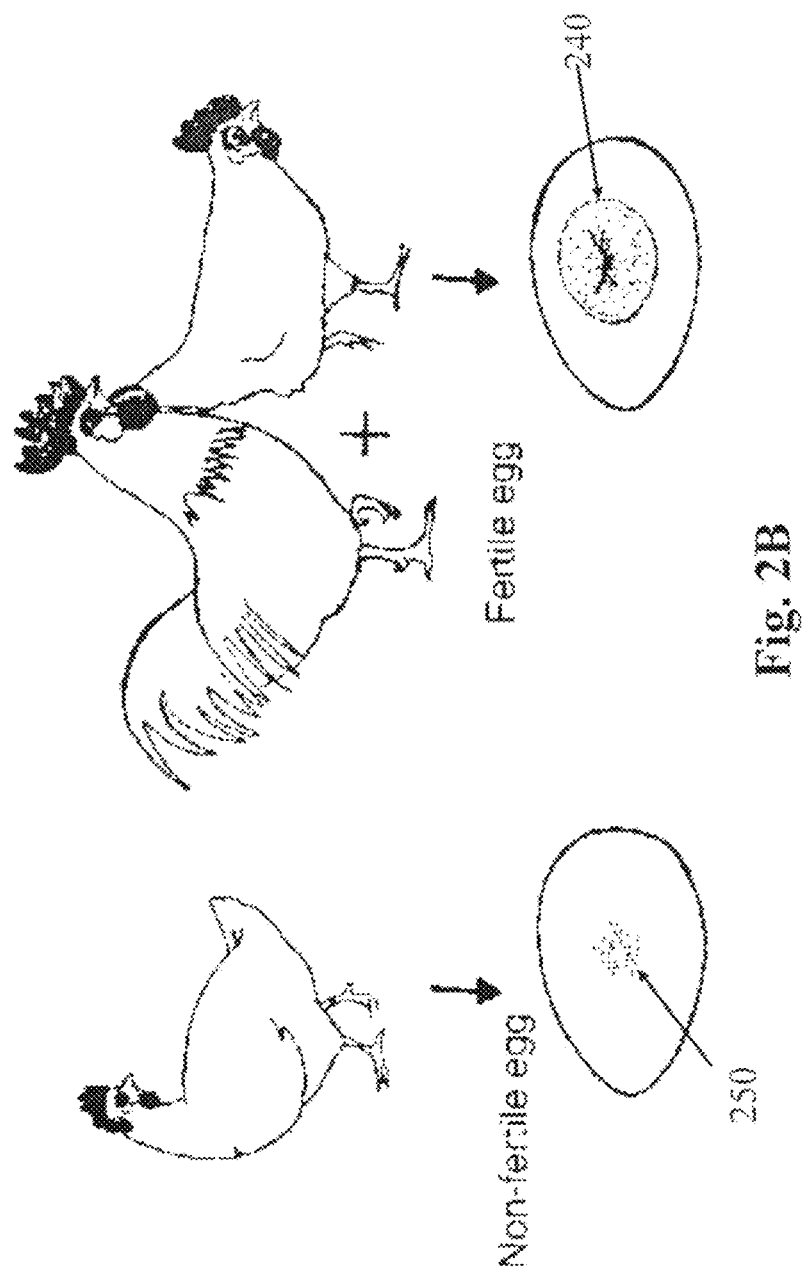
FIG. 2B is an illustration of fertile and not fertile eggs prior to incubation.

Reference is now made to FIG. 2B, which is an illustration of fertile and non-fertile eggs prior to incubation. As shown, there are differences between fertilized and non-fertilized eggs. For a fertilized egg, a body or structure starts forming in or close to day zero, indicated by arrow 240. In contrast, for a non-fertilized egg, a smaller body can be seen, as indicated by arrow 250, which represents a less significant growth or development. This trend is further developed and clarified as the time moves on.

According to some embodiments, the radar controller runs code for processing reflected signals, to determine, for example, egg fertility. For example, an algorithm may be used to determine a fertility score or indication on the basis of the shape of the reflection and the amplitude of the reflected wave, thereby enabling automated recognition of a fertile egg from a non-fertile one. In particular, fertile eggs and non-fertile eggs have different dielectric properties (e.g., that may be defined as a quantity measuring the ability of a substance to store electrical energy in an electric field), that may be discovered and processed by the radar controller, thereby distinguishing between fertile and non-fertile eggs According to some embodiments, a fertilization algorithm may be executed to determine when a selected and meaningful change in the dielectric properties of the target egg(s) occurs, thereby providing an indication of fertility on or dose to day zero after laying the egg. In one non-limiting example, the radar scan data processing may include one or more of time zero processing to remove the airwave gaps; hyperbola removing; and ringing removal.

Figure 2C:
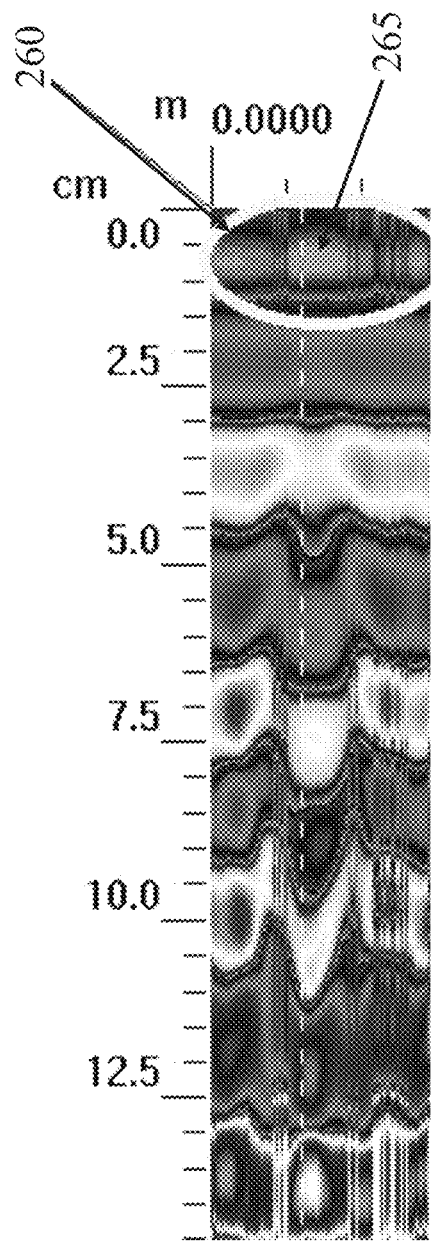
FIGS. 2C and 2D (in both colored and greyscale versions) are snapshots of scanning results resulting from two non-limiting examples of the application of a fertility scanning processing process, constructed and operative according to an embodiment of the disclosed technique.

As can be seen with reference to a scanning snapshot in FIG. 2C, as indicated by arrow 265, a fertile egg close to day zero can be identified by the thick and compact (green) line in the ringed area 260. This thicker line provides an indication of a body or formation being formed, thereby providing a stable or more sustainable dialectic in a certain area, associated with the formation of this body. In contrast, as can be seen with reference to a scanning snapshot in FIG. 2D, as indicated by arrow 275, a non-fertile egg close to day zero can be identified by the thinner (green) in the line in the ringed area 270, that tends to fade away as the antenna scans the leg of the egg. This thinner line 275 provides an indication of a lack of body or structure formation, thereby such an egg cannot provide a stable or sustainable dialectic in a certain area, associated with the formation of a growing body. Of course, other indicators of fertility may be used.

Figure 4:
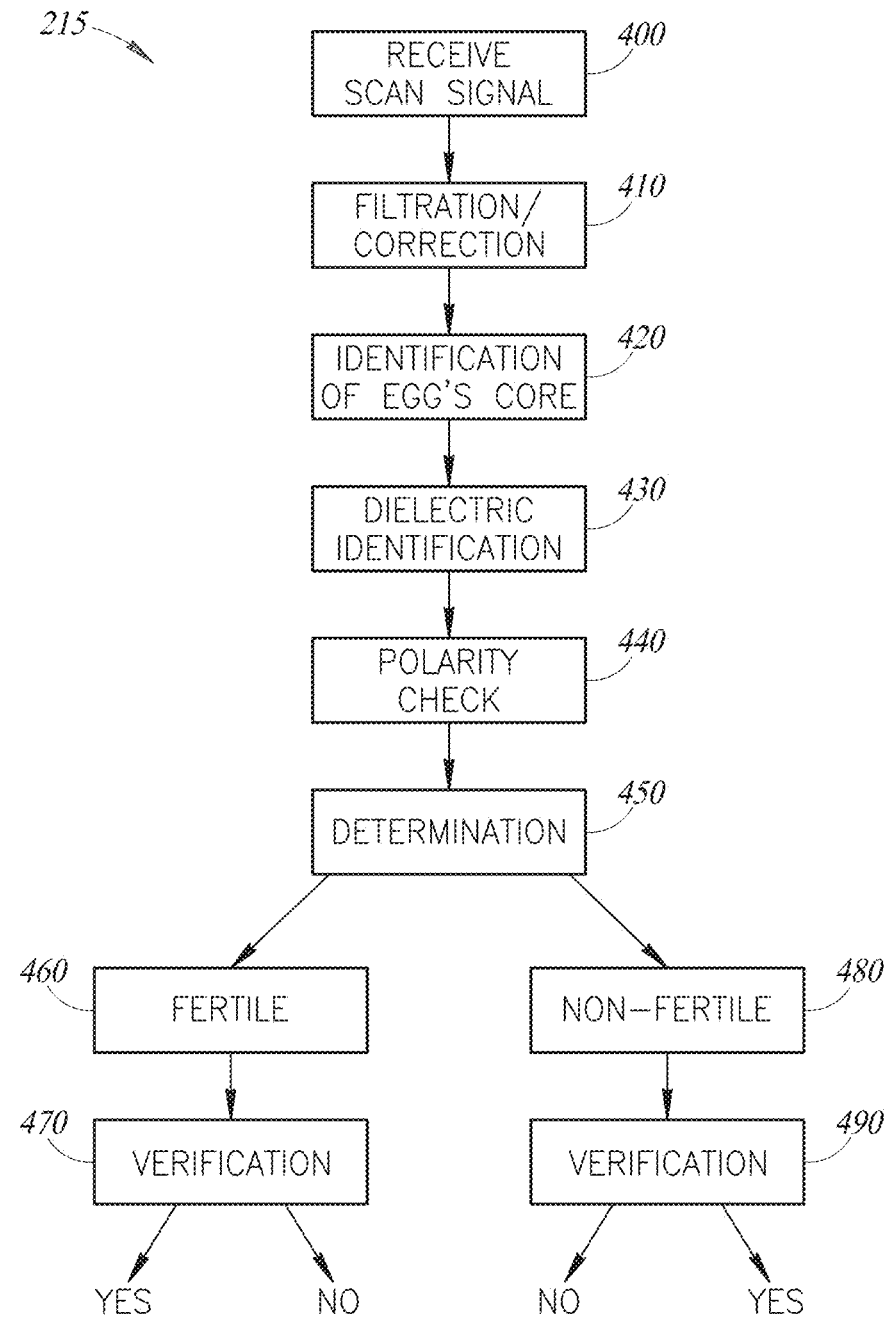
FIG. 4 is a flowchart illustrating the signal processing procedure, constructed and operative in accordance with an embodiment of the disclosed technique.

Reference is now made to FIG. 4 which is a flowchart illustrating the signal processing procedure (step 215 in FIG. 2A), constructed and operative in accordance with an embodiment of the disclosed technique. As stated above, radar controller 105 receives reflections of scanned waves from the radar antenna or receiver. Step 400 refers to receipt of these scanned waves (raw data) which will be referred to as scan signal 400. Scan signal 400 comprises reflections of waves from at least one egg including signals such as airwaves, hyperbolas and ringing. At step 410 entitled "filtration and/or correction", the scan signal is post processed by at least removing airwaves, migrating data or removing ringing. An embodiment of the procedure includes removing airwaves from the received scan signal by using time zero correction. In an additional embodiment of the processing procedure removing hyperbolas from received scan signal 400 is obtained by using migration. In a further embodiment of the processing procedure removing ringing from the received scan signal is obtained by using IIR filters (bandpass, background removal, stacking) or deconvolution filtering. In a preferred embodiment of the disclosed technique the step of removing airwaves is carried out before the step of removing ringing. In an additional embodiment of the disclosed processing procedure the step of removing ringing is carried out before or after the step of removing hyperbolas.

Figure 2D:
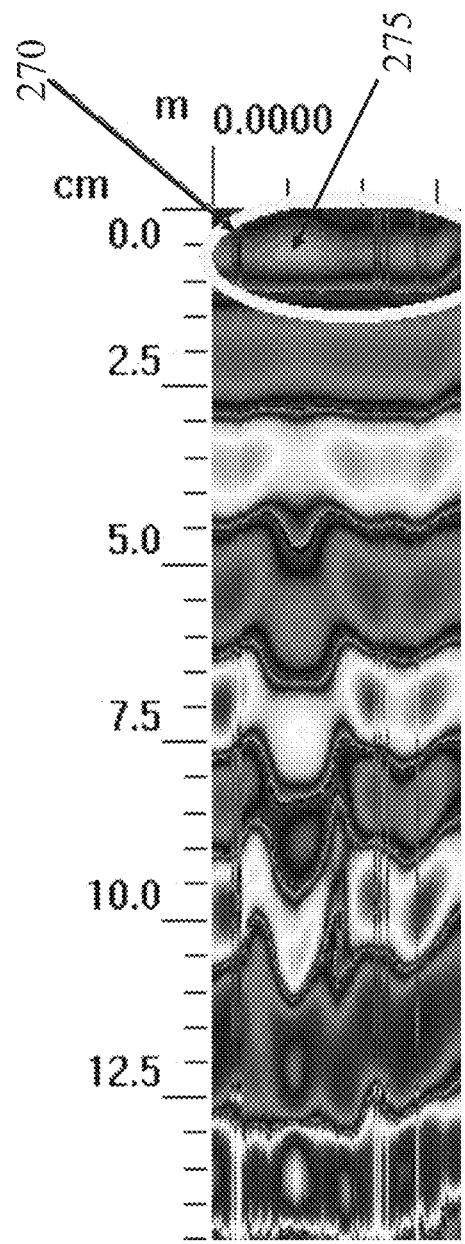

The filtered signal is then analyzed in step 420 to identify the core of the egg (indicated 260 or 270 in FIGS. 2C and 2D). In general, formation of a dense and thick section evidences fertility whereas a thin area with loose boundaries or no distinct borderlines evidences non-fertility. In one embodiment of the disclosed technique, step 430 includes dielectric identification of the core of the egg and is followed by a polarity check in step 440. However, in another embodiment of the disclosed technique the step of identification of the core of the egg (step 420) is carried out before, after or in parallel to steps 430 (dielectric identification) and 440 (the polarity check). In an additional embodiment of the disclosed technique the polarity check (step 440) is carried out before step 410 (filtration). The polarity of the filtered signal obtained after filtration 410 is also compared to absolute negative which is from air and absolute positive which is for metallic objects. The fertility usually comes at the lower parts of a positive reflection. A negative polarity implies a non-fertile egg and a positive polarity signifies fertile egg. Results of identification of the core of the egg, dielectric identification and polarity check are accumulated and a determination of fertile/non-fertile 450 is made.

In an alternative embodiment of the disclosed technique additional information such as for example, time passed from laying of the egg until scanning, can be combined with the above information in order to reach determination 450. Determination 450 of positive/fertile egg 460 is further verified (step 470) in conjunction with reference database including fertile and non-fertile information. Similarly, a determination of a negative/non-fertile egg 480 is further verified (step 490) with reference database including fertile and non-fertile information. At the end of verification steps 470 and 490, results with probability larger than 90%, whether the eggs are fertile or not are obtained.

Figure 5:
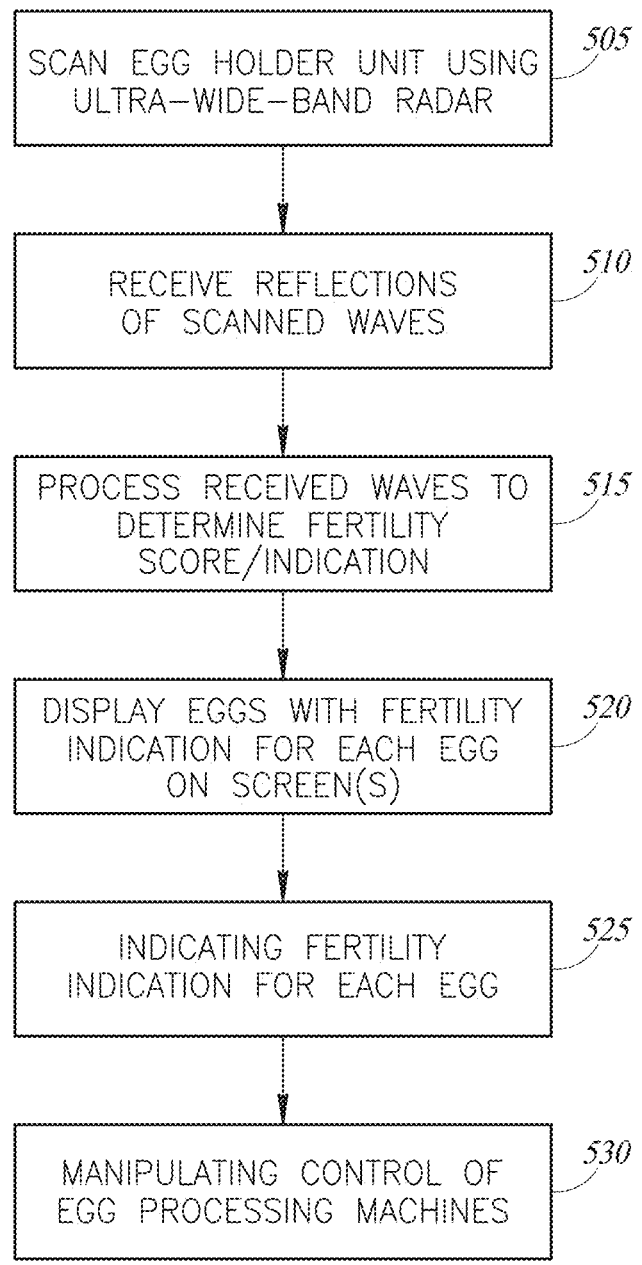
FIG. 5 is a flowchart illustrating a non-invasive method for detecting the fertility condition of an avian egg, constructed and operative in accordance with another embodiment of the disclosed technique.

Reference is now made to FIG. 5, which is a flowchart illustrating a non-invasive method for detecting the fertility condition of an avian egg, constructed and operative in accordance with another embodiment of the disclosed technique. According to this embodiment, once the scanning 505 of an egg holding unit commences, as the eggs pass by the scanner or transceiver, the reflection from the inner part of the egg is received by the antennas (step 510). This refection is processed in step 515 and sent to the viewer or screen for the user to see and optionally control the egg detection process. Displaying eggs with fertility indication for each egg on screen(s) in step 520 enables a user to monitor the eggs during the procedure. In the disclosed embodiment, the system is integrated with the egg sorting or detection machinery to mark fertile and/or non-fertile eggs. After providing a marking or any other indication for each egg at step 525, manipulating controls are instructed to remove the unwanted eggs from the is production line i.e. from the egg holding unit or the tray (step 530). For example, radar controller 105 may be configured to interface with existing or new egg sorting or processing machinery, to instruct or manage such machinery in accordance with the radar controller processing. In some embodiments, the radar controller may integrate with existing egg separation or processing technologies known in the industry.

A further embodiment of the disclosed technique relates to a non-invasive method for detecting the fertility condition of an avian egg. The method comprises the following steps: radar scanning at least one egg, wherein at least one radar transmitter transmits waves and a radar receiver receives a scan signal comprising reflections of the waves from the at least one egg. Thereafter, processing the received scan signal to determine a fertility indication for the at least one egg. The processing procedure comprises removal of unwanted signals from the received scan signal thereby outputting a filtered signal. The unwanted signals include at least one of airwaves, hyperbolas and ringing. The following procedure is analyzing the filtered signal to determine correlation with at least one reference marker evidencing fertility or non-fertility of an egg to determine a fertility indication. Then, the method provides a fertility indication for each egg scanned.

It will be appreciated by persons skilled in the art that the disclosed technique is not limited to what has been particularly shown and described hereinabove. Rather the scope of the disclosed technique is is defined only by the claims, which follow.

The invention claimed is:

1. A system for non-invasively determining the fertility of an avian egg prior to incubation, comprising:
   an egg holding unit in which at least one egg is positioned;
   at least one radar transmitter, operative for transmitting electromagnetic radar waves towards said at least one egg;
   at least one radar receiver for receiving a received signal, including at least a portion of said electromagnetic radar waves after passing through said at least one egg placed within said egg holding unit;
   a processor adapted to analyze said received signal according to a predetermined fertility determination procedure; and
   a communication interface for providing a fertility indication with respect to each one of said at least one egg.

2. The system for non-invasively determining the fertility of an avian egg according to claim 1, wherein said communication interface for providing fertility indication for each of said at least one egg includes a display device coupled with said communication interface, operative to show fertilization data obtained from said processor.

3. The system for non-invasively determining the fertility of an avian egg according to claim 2, wherein said display device uses a graphical user interface (GUI) and provides said fertilization data to one or more end users.

4. A system for non-invasively determining the fertility of an avian egg according to claim 1, wherein said system further comprises means coupled with said communication interface, operative for marking digitally and/or mechanically at least some of said at least one egg scanned thereby, said marking indicating fertility or non-fertility of said egg.

5. The system for non-invasively determining the fertility of an avian egg according to claim 1, wherein said at least one radar transmitter is coupled with at least one antenna.

6. The system for non-invasively determining the fertility of an avian egg according to claim 1, wherein said at least one radar receiver is coupled with at least one antenna.

7. The system for non-invasively determining the fertility of an avian egg according to claim 1, further comprising at least one reflector, operative to reflect at least a portion of said electromagnetic radar waves towards said at least one radar receiver.

8. The system for non-invasively determining the fertility of an avian egg according to claim 7, wherein said at least one reflector is planar.

9. The system for non-invasively determining the fertility of an avian egg according to claim 7, wherein said at least one reflector is curved.

10. An egg holding unit constructed for containing at least one avian egg, said egg holding unit comprising an outer casing; and an inner casing, wherein said egg holding unit is adapted to selectively reflect radar signals transmitted by a radar transmitter, from the eggs to at least one radar receiver collecting electromagnetic wave reflections from multiple eggs.

11. A non-invasive method for detecting the fertility condition of avian eggs prior to incubation, comprising the steps of:

a. transmitting electromagnetic radar waves by a plurality of radar transmitters positioned around said eggs towards said eggs and receiving at least a portion of said electromagnetic radar waves by a radar receiver after passing through said eggs;
b. processing said at least portion of said electromagnetic radar waves by a processor to determine a fertility indication for said eggs; and
c. providing a fertility indication for each egg scanned.

12. A non-invasive method for detecting the fertility condition of avian eggs according to claim 11, wherein removal of unwanted signals from said received scan signal comprises: removing airwaves, removing hyperbolas, or removing ringing.

13. A non-invasive method for detecting the fertility condition of avian eggs according to claim 12, wherein removing air waves from said received scan signal is obtained by using time zero correction.

14. A non-invasive method for detecting the fertility condition of avian eggs according to claim 12, wherein removing hyperbolas from said received scan signal is obtained by using migration.

15. A non-invasive method for detecting the fertility condition of avian eggs according to claim 12, wherein removing ringing from said received scan signal is obtained by using MR filters (bandpass, background removal, stacking) or deconvolution filtering.

16. A non-invasive method for detecting the fertility condition of avian eggs according to claim 12, wherein the step of removing airwaves is carried out before the step of removing ringing.

17. A non-invasive method for detecting the fertility condition of avian eggs according to claim 12, wherein the step of removing ringing is carried out before or after the step of removing hyperbolas.

18. A non-invasive method for detecting the fertility condition of avian eggs according to claim 11, further comprising the step of: providing a digital and/or mechanical fertility indication for each egg scanned.

19. A non-invasive method for detecting the fertility condition of avian eggs according to claim 11, further comprising the step of: displaying the eggs with fertility indication on one or more screens.

20. A non-invasive method for detecting the fertility condition of avian eggs according to claim 11, further comprising the step of: a user interacting with the egg processing machines to stop the machines, zoom in or out, mark an egg, remove an egg, add notes, and send alerts.

21. The system for non-invasively determining the fertility of an avian egg according to claim 1, wherein said processor determines fertility by:
   removing unwanted signals from said received scan signal thereby outputting a filtered signal; and
   analyzing said filtered signal to determine correlation with at least one reference marker evidencing fertility or non-fertility of an egg to determine a fertility condition.

22. The non-invasive method for detecting the fertility condition of avian eggs according to claim 11, wherein said processing comprises:
   removal of unwanted signals from said received scan signal thereby outputting a filtered signal; and
   analyzing said filtered signal to determine correlation with at least one reference marker evidencing fertility or non-fertility of an egg to determine a fertility condition.

* * * * *